United States Patent [19]

Cragoe, Jr. et al.

[11] Patent Number: 4,463,208
[45] Date of Patent: Jul. 31, 1984

[54] TREATMENT OF GRAY MATTER EDEMA

[75] Inventors: Edward J. Cragoe, Jr., Lansdale, Pa.; Robert S. Bourke, Slingerlands, N.Y.

[73] Assignee: Merck & Co., Inc., Rahway, N.J.

[21] Appl. No.: 474,659

[22] Filed: Mar. 11, 1983

Related U.S. Application Data

[63] Continuation-in-part of Ser. No. 336,107, Dec. 30, 1981, , which is a continuation of Ser. No. 184,590, Sep. 5, 1980, abandoned, which is a continuation of Ser. No. 57,637, Jul. 16, 1979, abandoned, which is a continuation of Ser. No. 880,256, Feb. 22, 1978, abandoned.

[51] Int. Cl.³ .............................................. C07C 69/76
[52] U.S. Cl. .................................................... 562/462
[58] Field of Search .......................... 562/462; 560/53

[56] References Cited

U.S. PATENT DOCUMENTS

| | | | |
|---|---|---|---|
| 3,668,241 | 6/1972 | Cragoe et al. | 424/308 |
| 3,704,314 | 11/1972 | Cragoe et al. | 424/308 |
| 3,984,465 | 10/1976 | Cragoe et al. | 424/308 |
| 4,070,539 | 1/1978 | Cragoe et al. | 424/308 |

OTHER PUBLICATIONS

Long et al., Dynamics of Brain Edema, pp. 293–300, Springer-Verlag, (1976).
Bourke et al., "Dynamic Properties of Glial Cells" Int'l. Symposium, E. Schoffenels et al., Eds. pp. 337–346, Pergamon Press Oxford, 1978.
Bourke et al., Brain Research, 105, 309–323, (1976).
Cragoe et al., J. Med. Chem., 25, 567–569, (1982).

Primary Examiner—Paul J. Killos
Attorney, Agent, or Firm—W. H. Nicholson; M. A. Monaco; T. E. Arther

[57] ABSTRACT

The invention relates to the treatment of gray matter edema in the brain or spinal cord by the administration of (indanyloxy)acetic acids, and analogs and salts thereof.

2 Claims, No Drawings

TREATMENT OF GRAY MATTER EDEMA

RELATED APPLICATIONS

This is a continuation-in part of application, Ser. No. 336,107 filed Dec. 30, 1981, which is a continuation of Ser. No. 184,590, filed Sept. 5, 1980, now abandoned; which in turn is a continuation of Ser. No. 57,637, filed July 16, 1979, now abandoned; which in turn is a continuation of Ser. No. 880,256, filed Feb. 22, 1978, also abandoned.

BACKGROUND OF THE INVENTION

Traumas to the brain caused by outside physical forces acting on the skull or spinal cord (hereinafter, head or spine injury), ischemic stroke, Reye's syndrome, post-operative brain surgery trauma and hydrocephalus are all characterized by edema and resultant swelling. The standard treatment has been the administration of steroids, because of their known anit-inflammatory activity or procedures such as the insertion of a shunt in the case of progressive hydrocephalus. Diuretics have not found much use in the treatment of brain and spinal cord edema partly because the blood-brain barrier prevents adequate concentrations of the diuretics from reaching brain cells. Thus, any decrease in edema following diuretic administration would be a secondary or independent effect resulting from general electrolyte loss and resultant dehydration of the rest of the body. Such dehydration would be inappropriate to someone with a traumatized brain or spinal cord.

Long, et al., *Dynamics of Brain Edema*, pp. 293-300, Springer-Verlag (1976) described the use of the diuretics furosemide and acetazolamide for the treatment of certain models of brain edema in cats.

Bourke, et al., *Brain Research*, 105 (1976) 309-323 described the effect of the diuretics ethacrynic acid and acetazolamide on swelling of monkey cerebrocortical slices.

SUMMARY OF THE INVENTION

The invention comprises the treatment of persons with gray matter edema. This edema can be the result of any of a variety of causes; for example from external physical forces, such as a blow to the head, neck or spine, a motor vehicle accident, or a fall, from ischemic stroke, from hydrocephalus, or from radiation. The treatment comprises administering to such a person an effective amount of a compound of the formula:

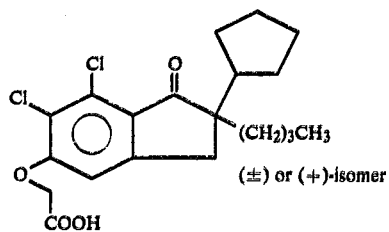

I which is (±) or (+) [(-2-butyl-6,7-dichloro-2-cyclopentyl-2,3-dihydro-1-oxo-1H-inden-5-yl)oxy]acetic acid Included within the scope of this invention is the use of the salts, esters and amide derivatives of formula I, which are prepared by conventional methods, well-known to those skilled in the art. Thus, for example, the ester derivatives may be prepared by the reaction of the compound of formula I of this invention with an alcohol, for example, with a lower alkanol.

The amide derivatives may be prepared by converting a compound of formula I to its corresponding acid chloride by treatment with thionyl chloride followed by treating said acid chloride with ammonia, an appropriate mono-lower alkyl amine, di-lower alkyl amine or a hetero amine, such as piperidine, morpholine and the like, to produce the corresponding amide compound. These and other equivalent methods for the preparation of the salts, esters, and amide derivatives of the instant products will be apparent to one having ordinary skill in the art and to the extent that said derivatives are both non-toxic and pharmacologically acceptable, said derivatives are the functional equivalent of the corresponding compound of formula I.

The preferred salts are those with sodium, potassium, ammonia, ethanolamine, diethanolamine, triethanolamine, N-methylpiperazine, piperazine, cyclohexylamine, and the like.

Inasmuch as there is a wide variety of symptoms and severity associated with gray matter edema, particularly when it is caused by blows to the head or spinal cord, the precise treatment protocol is left to the practitioner. It is up to the practitioner to determine the patient's response to treatment and to vary the dosages accordingly. A recommended dosage range is from 1 $\mu$g to 2 mg/kg of body weight as a primary dose and a sustaining dose of half to equal the primary dose, every 12 to 24 hours.

The compound of this invention can be administered by a variety of established methods, including intravenously, intramuscularly, subcutaneously, and orally. As with dosage, the precise mode of administration is left to the discretion of the practitioner.

Studies on human pathological tissues have revealed that ischemic insult to the brain is a major concomitant of head injury.

Recent studies in experimental head injury by R. S. Bourke et al. (R. S. Bourke, M. A. Daze' and H. K. Kimelberg, "Dynamic Properties of Glial Calls, International Symposium, E. Schoffeniels et al., Eds., pp. 337-346, Pergamon Press, Oxford, 1978 and references cited therein) and experimental stroke by J. H. Garcia et al. (J. H. Garcia, H. Kalimo, Y. Kamijyo and B. F. Trump, *Virchows Archive*. B, 25, 191, (1977), indicate that astroglial swelling, a secondary and potentially inhibitable process, is a fundamental pathophysiological response to ischemic/traumatic brain insult in both pathological disorders. Furthermore, astroglial swelling is believed to reduce oxygen available to neurons by prolongation of the oxygen diffusion pathway. Thus, the damage to cerebral grey matter may be far more extensive as a result of pathological events secondary to astroglial swelling than as a result of damage inflicted by the initial ischemic/traumatic insult. Consequently, it is of prime importance that the treatment commense as soon as possible after the initial trauma in order to minimize the brain cell damage and the possibility of death or permanent paralysis.

One aspect of this invention is the treatment of persons with gray matter edema by concomitant administration of the compound of formula I or a pharmaceutically acceptable salt, ester, or amide thereof and of anti-inflammatory steroids. These steroids are of some, albeit limited, use in control of white matter edema associated with ischemic stroke and head injury. Steroid therapy is given according to established practice as a supplement to the compound of formula I as taught elsewhere herein.

The compound of formula I is utilized by formulating it in a composition such as tablet, capsule or elixir for oral administration. Sterile solutions or suspensions can be used for parenteral administration. About 70 μg to 150 mg of a compound or mixture of compound of formula I or a physiologically acceptable salt, ester, or amide is compounded with a physiologically acceptable vehicle, carrier, excipient, binder, preservative, stabilizer, flavor, etc., in a unit dosage form as called for by accepted pharmaceutical practice. The amount of active substance in the composition is such that dosage in the range indicated is obtained.

Illustrative of the adjuvants which may be incorporated in tablets, capsules and the like are the following: a binder such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent, such as sucrose lactose, or saccharin; a flavoring agent, such as peppermint, oil of wintergreen or cherry. When the dosage unit form is a capsule, it may contain in addition to materials of the above type a liquid carrier such as a fatty oil. Various other materials may be present as coatings or to otherwise enhance the pharmaceutical elegance of the preparation. For instance, tablets may be coated with shellac, sugar or the like. A syrup or elixir may contain the active compound, surcrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a conventional vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples are included to illustrate the preparation of representative dosage forms and the compound of formula I.

EXAMPLE 1

[2-Butyl-6,7-dichloro-2-cyclopentyl-2,3-dihydro-1-oxo-1H-inden-5-yl)oxy]acetic acid Step A: Preparation of 2-Butyl-6,7-dichloro-2-cyclopentyl-2,3-dihydro-5-methoxy-1H-inden-1-one A solution of 6,7-dichloro-2-cyclopentyl-2,3-dihydro-5-methoxy-1H-inden-1-one (7.2 g) in benzene (70 ml) was heated at reflux in a $N_2$ atmosphere and treated over a 5 minute period with a solution of potassium t-butoxide (4.2 g) in t-butanol (70 ml). The solution was refluxed for ¾ hour, treated with butyl iodide (11 ml), refluxed for an additional ¾ hour, cooled, treated with water (50 ml) and the organic solvents were distilled at reduced pressure. The aqueous slurry was extracted with ether washed with water, dried over $MgSO_4$ and evaporated at reduced pressure. Treatment of the residue with hexane (100 ml) gave 6.9 g of 2-butyl-6,7-dichloro-2-cyclopentyl-2,3-dihydro-5-methoxy-1H-inden-1-one, m.p. 122°–123° C.

Step B: Preparation of 2-Butyl-6,7-dichloro-2-cyclopentyl-2,3-dihydro-5-hydroxy-1H-inden-1-one To pyridine hydrochloride (50 g) fused at 190° C. was added 2-butyl-6,7-dichloro-2-cyclopentyl-2,3-dihydro-5-methoxy-1H-inden-1-one (6.6 g). The reaction mixture was stirred at 190° C. in an inert atmosphere for 1½ hours then poured onto ice water. The resulting solid was dissolved in ether, washed with water, dried over $MgSO_4$, evaporated at reduced pressure then triturated with hexane (50 ml) to give 5.5 g of 2-butyl-6,7-dichloro-2-cyclopentyl-2,3-dihydro-5-hydroxy-1H-inden-1-one, m.p. 159.5°–160° C.

Step C: Preparation of [(2-Butyl-6,7-dichloro-2-cyclopentyl-2,3-dihydro-1-oxo-1H-inden-5-yl)oxy]acetic acid A mixture of 2-butyl-6,7-dichloro-2-cyclopentyl-2,3-dihydro-5-hydroxy-1H-inden-1-one (4 g), potassium carbonate (1.8 g), and ethyl bromoacetate (1.5 ml) in dimethylformamide (40 ml) was heated with stirring at 60°–65° C. for 3 hours. A solution of potassium hydroxide (1.5 g) in methanol (20 ml) was added and the reaction mixture was refluxed for 2½ hours. The solution was poured into ice water and excess hydrochloric acid, extracted with ether, washed with water and dried over $MgSO_4$. The ether was evaporated and the residue was crystallized from a mixture of dichloromethane and 1-chlorobutane (1:1) to give [(2-butyl-6,7-dichloro-2-cyclopenyl-2,3-dihydro-1-oxo-1H-inden-5-yl)oxy]acetic acid, m.p. 180°–181° C.

EXAMPLE 2

(+)- [2-Butyl-6,7-dichloro-2-cyclopentyl-2,3-dihydro-1-oxo-1H-inden-5-yl)oxy]acetic acid A mixture of racemic 4-[(2-butyl-6,7-dichloro-2-cyclopentyl-2,3-dihydro-1-oxo-1H-inden-5-yl)oxy]acetic acid (26.1 g, 0.065 mole) and cinchonine (19.2 g, 0.065 mole) were dissolved in hot dimethylformamide (400 ml). The resulting salt was recrystallized 10 times from dimethylformamide then partitioned between aqueous hydrochloric acid and ether. The ether extract was washed with dilute hydrochloric acid and water then dried over anhydrous magnesium sulfate. Evaporation of the ether gave 5.7 g of (+)- [2-butyl-6,7-dichloro-2-cyclopentyl-2,3-dihydro-1-oxo-1H-inden-5-yl)oxy]acetic acid which melts at 173°–4° C. $[\alpha]_D^{24} + 19.1°$ (C 5, EtOH).

Analysis for $C_{20}H_{24}Cl_2O_4$:
Calc: C, 60.16; H, 6.06;
Found C, 60.48; H, 6.35.

EXAMPLE 3

Dry-filled capsules containing 50 mg of active ingredient per capsule

|  | Per Capsule |
|---|---|
| (+)-[2-Butyl-6,7-dichloro-2-cyclopentyl-2,3-dihydro-1-oxo-1H—inden-5-yl)oxy]acetic acid Lactose | 50 mg |
| Magnesium Stearate | 149 mg |
| Capsule (Size No. 1) | 1 mg |
|  | 200 mg |

(+)-[2-Butyl-6,7-dichloro-2-cyclopentyl-2,3-dihydro-1-oxo-1H-inden-5-yl)oxy]acetic acid is reduced to a No. 60 powder and then lactose and magnesium stearate are passed through a No. 60 bolting cloth onto the powder and the combined ingredients admixed for 10 minutes and then filled into a No. 1 dry gelatin capsule.

EXAMPLE 4

Parenteral Solution of Sodium (+)-[2-Butyl-6,7-dichloro-2-cyclopentyl-2,3-dihydro-1-oxo-1H-inden-5-yl)oxy]acetic acid 100 Mg of (+)-[2-butyl-6,7-dichloro-2-cyclopentyl-2,3-dihydro-1-oxo-1H-inden-5-yl)oxy]acetic acid are dissolved in 3 ml. of 0.1 N-sodium hydrogen carbonate solution. The solution is made up to 10 ml with water and sterilized.

EXAMPLE 5

Parenteral Solution of Sodium [2-Butyl-6,7-dichloro-2-cyclopentyl-2,3-dihydro-1-oxo-1H-inden-5-yl)oxy]acetic acid 100 Mg of [2-butyl-6,7-dichloro-2-cyclopentyl-2,3-dihydro-1-oxo-1H-inden-5-yl)oxy]acetic acid are dissolved in 3 ml of 0.1N-sodium hydrogen carbonate solution. The solution is made up to 10 ml with water and sterilized.

EXAMPLE 6

Dry-filled capsules containing 50 mg of active ingredient per capsule

|  | Per Capsule |
|---|---|
| Racemic [2-butyl-6,7-dichloro-2-cyclopentyl-2,3-dihydro-1-oxo-1H—inden-5-yl)oxy]acetic acid |  |
| Lactose | 50 mg |
| Magnesium stearate | 149 mg |
| Capsule (Size No. 1) | 1 mg |
|  | 200 mg |

Racemic [2-butyl-6,7-dichloro-2-cyclopentyl-2,3-dihydro-1-oxo-1H-inden-5-yl)oxy]acetic acid is reduced to a No. 60 powder and then lactose and magnesium stearate are passed through a No. 60 bolting cloth onto the powder and the combined ingredients admixed for 10 minutes and then filled into a No. 1 dry gelatin capsule.

What is claimed is:

1. The compound, (±)- or (+)- [2-butyl-6,7-dichloro-2-cyclopentyl-2,3-dihydro-1-oxo-1H-inden-5-yl)oxy]acetic acid.

2. The compound of claim 1 which is the (+)-isomer.

* * * * *